United States Patent
Iyengar et al.

(10) Patent No.: US 10,488,359 B2
(45) Date of Patent: Nov. 26, 2019

(54) METHOD AND APPARATUS FOR ENCODING TEST STRIPS

(71) Applicant: AGAMATRIX, INC., Salem, NH (US)

(72) Inventors: Sridhar Iyengar, Salem, NH (US); Charles Boiteau, Carlisle, MA (US); Martin Forest, Nashua, NH (US); Colin Butters, Pelham, NH (US)

(73) Assignee: AgaMatrix, Inc., Salem, NH (US)

( * ) Notice: Subject to any disclaimer, the term of this patent is extended or adjusted under 35 U.S.C. 154(b) by 755 days.

(21) Appl. No.: 14/871,650

(22) Filed: Sep. 30, 2015

(65) Prior Publication Data

US 2016/0061763 A1    Mar. 3, 2016

Related U.S. Application Data (62) Division of application No. 13/823,650, filed as application No. PCT/US2011/051983 on Sep. 16, 2011, now Pat. No. 9,176,091.

(Continued)

(51) Int. Cl.
*G01N 27/327* (2006.01)
*G01N 33/487* (2006.01)
(Continued)

(52) U.S. Cl.
CPC .......... *G01N 27/3272* (2013.01); *A61B 5/05* (2013.01); *C12Q 1/00* (2013.01); *G01N 27/327* (2013.01); *G01N 27/3273* (2013.01); *G01N 33/48771* (2013.01); *A61B 5/14* (2013.01); *A61B 5/150022* (2013.01)

(58) Field of Classification Search
CPC .......... G01N 27/3272; G01N 27/3273; G01N 27/327; G01N 33/48771; C12Q 1/00; A61B 5/05; A61B 5/150022; A61B 5/14
See application file for complete search history.

(56) References Cited

U.S. PATENT DOCUMENTS

| | | |
|---|---|---|
| 4,714,874 A | 12/1987 | Morris et al. |
| 5,243,516 A | 9/1993 | White |

(Continued)

FOREIGN PATENT DOCUMENTS

| | | |
|---|---|---|
| EP | 2067865 A1 | 6/2009 |
| WO | 2000/033074 A1 | 6/2000 |

*Primary Examiner* — Jeffrey T Barton
*Assistant Examiner* — Michael Y Sun
(74) *Attorney, Agent, or Firm* — Larson & Anderson, LLC (57) ABSTRACT

A test meter for receiving a test strip comprises:
 (a) a housing;
 (b) electronic circuitry disposed within the housing and
 (c) a strip port connector connected to the electronic circuitry and extending to an opening in the housing, said strip port connector connecting the electronic circuitry with a received test strip. The strip port connector contains a pair of top and bottom contacts, said top and bottom contacts having a proximal end and a distal end and a central contact portion, the top and bottom contacts of the pair are transversely aligned with one another; and the distal ends of the top and bottom contacts are separated or separable from one another by insertion of a test strip between the opposed contacts. The contacts and the meter are adapted to permit detection of faulty contacts and/or coding associated with an inserted test strip.

11 Claims, 11 Drawing Sheets

Related U.S. Application Data (60) Provisional application No. 61/383,896, filed on Sep. 17, 2010.

(51) Int. Cl.
*C12Q 1/00* (2006.01)
*A61B 5/05* (2006.01)
*A61B 5/145* (2006.01)
*A61B 5/15* (2006.01)

(56) References Cited

U.S. PATENT DOCUMENTS

| | | |
|---|---|---|
| 5,352,351 A | 10/1994 | White et al. |
| 5,942,102 A | 8/1999 | Hodges et al. |
| 6,071,391 A | 6/2000 | Gotoh et al. |
| 6,284,125 B1 | 9/2001 | Hodges et al. |
| 6,377,894 B1 | 4/2002 | Deweese et al. |
| 6,662,439 B1 | 12/2003 | Bhullar |
| 6,773,671 B1 | 8/2004 | Lewis et al. |
| 7,090,764 B2 | 8/2006 | Iyengar et al. |
| 7,344,626 B2 | 3/2008 | Harding et al. |
| 7,501,052 B2 | 3/2009 | Iyengar et al. |
| 7,517,439 B2 | 4/2009 | Harding et al. |
| 7,527,716 B2 | 5/2009 | Harding et al. |
| 7,547,382 B2 | 6/2009 | Harding et al. |
| 7,601,249 B2 | 10/2009 | Iyengar et al. |
| 7,601,299 B2 | 10/2009 | Beaty et al. |
| 7,625,473 B2 | 12/2009 | Hsu |
| 7,645,374 B2 | 1/2010 | Diamond et al. |
| 7,645,421 B2 | 1/2010 | Groll |
| 7,695,608 B2 | 4/2010 | Kim et al. |
| 7,713,392 B2 | 5/2010 | Harding et al. |
| 7,771,583 B2 | 8/2010 | Diamond et al. |
| 7,780,827 B1 * | 8/2010 | Bhullar ............ G01N 33/48771 204/403.01 |
| 2005/0009126 A1 | 1/2005 | Andrews et al. |
| 2005/0258050 A1 * | 11/2005 | Harding ................ C12Q 1/004 205/775 |
| 2007/0015286 A1 | 1/2007 | Neel et al. |
| 2007/0110615 A1 * | 5/2007 | Neel ................ G01N 33/48771 422/400 |
| 2008/0229850 A1 * | 9/2008 | Huang ............ G01N 33/48771 73/866 |
| 2009/0095623 A1 | 4/2009 | Boiteau et al. |
| 2009/0138207 A1 | 5/2009 | Cosentino et al. |

* cited by examiner

Fig. 17D

METHOD AND APPARATUS FOR ENCODING TEST STRIPS

STATEMENT OF RELATED CASES

This application claims the benefit of U.S. Provisional Application No. 61/383,896 filed Sep. 17, 2010, which application is incorporated herein by reference for all purposes in countries permitting such incorporation.

BACKGROUND OF THE INVENTION

This application relates to test strips that are used in chemical assays in conjunction with a test meter and to combinations of tests strips and meters. The application further relates to a method of providing information about the test strip in coded format on the test strip so that it can be read by an associated meter.

Electrochemical test meters are known in the art, for example for the determination of blood glucose levels. See, for example, U.S. Pat. Nos. 7,771,583; 7,645,374; 7,601,249; 7,547,382; 7,517,439; 7,501,052; 7,344,626; 7,090,764; 6,662,439; 6,284,125; 6,071,391; 5,942,102; 5,352,351: and 5,243,516, all of which are incorporated herein by reference.

Methods for encoding information on disposable test strips are discussed in U.S. Pat. Nos. 7,713,392; 7,695,608; 7,645,421; 7,625,473; 7,601,299; and 4,714,874 which are incorporated herein by reference.

Strip port connector designs are discussed in U.S. Pat. Nos. 7,780,827 and 7,527,716, which are incorporated herein by reference.

SUMMARY OF THE INVENTION

The present invention provides a test meter for receiving a test strip comprising:
(a) a housing;
(b) electronic circuitry disposed within the housing and
(c) a strip port connector connected to the electronic circuitry and extending to an opening in the housing, said strip port connector connecting the electronic circuitry with a received test strip. The strip port connector contains a pair of top and bottom contacts, said top and bottom contacts having a proximal end and a distal end and a central contact portion, the top and bottom contacts of the pair are transversely aligned with one another; and the distal ends of the top and bottom contacts are separated or separable from one another by insertion of a test strip between the opposed contacts.

In the invention, the following features, can be employed in any combinations with each other that are not mutually exclusive.

In some embodiments, the distal ends of the top and bottom contacts are biased such that the central portions of the contacts are in electrical contact within one another when no test strip is received in the meter, which allows the electronic circuitry tests for electrical contact between the pair of top and bottom contacts at one or more times when a test strip is not received in the test meter. This test can be performed once, or more than one time.

In some embodiments, the strip port connector receives the test strip through one longitudinal end of the strip port connector.

In some embodiments, one of the top or bottom contacts is connected to the electronic circuitry to read encoding marks disposed on one surface of a test strip, and the other of the top or bottom contacts is connected to the electronic circuitry to obtain information about measurements made by the test strip on a sample introduced into the test strip.

In some embodiments, one of the top and bottom contacts is a flexible bent spring, and the other of the top and bottom contacts is a flat contact surface. In some of these embodiments, the housing comprises a ledge adjacent to the distal end of the flexible bent spring contact, said ledge limiting deflection of the adjacent contact in the event spring forces of the top and bottom contacts are mismatched.

In some embodiments, the test meter comprises at least one additional pair of contacts in the strip port connector, wherein
  each of the additional pairs of contacts includes an additional top and an additional bottom contact, said additional top and bottom contacts having a proximal end and a distal end and a central contact portion;
  the additional top and bottom contacts of each the additional pair are transversely aligned with one another; and
  the distal ends of the additional top and bottom contacts of each additional pair are separable from one another by insertion of a test strip between the opposed additional contacts.

BRIEF DESCRIPTION OF THE DRAWINGS

FIGS. 11 A-C show embodiments of conductive patterns that can be utilized for the encoding pads 106 in test strips according to the invention.

FIGS. 13 A-D show embodiments of conductive patterns for the connector tabs of the invention with and without notching.

FIGS. 14 A-C show the conductive patterns for the top and bottom surfaces of a test strip in accordance with the invention.

FIGS. 15 A and B show the conductive patterns for the top and bottom surfaces of a test strip in accordance with the invention.

DETAILED DESCRIPTION OF THE INVENTION

The present application provides a test meter, and a test strip, and a method for using a combination of the test meter and the test strip in the determination of an analyte. These include meter embodiments that allow for testing the integrity of contacts within the strip port connector, meter and strip embodiments that enhance the amount of encoded information that can be provided to the meter by the strip, and combinations thereof. The application also relates to a method for testing the integrity of contacts within a strip port connector of a test meter.

The features of the meter and test strips described below can be used in combination with other meter features, including user interface, communications and signal processing features; and test strip configurations and chemistries known for use in electrochemical analyte test meters, and in particular for use in electrochemical glucose test systems.

Test strips often have information associated with them, such as:
  Calibration code for that batch,
  Regional coding or country coding,
  Product identification,
  Customer identification,
  Assay type (e.g. glucose test strip or ketone test strip), and
  Date of manufacture.
It would be easier for the user and less error prone if the test strip had information encoded onto it so that the user does not have to check and or enter the information into a device (meter) that would accept the test strip. However, many times, the information that the strip needs to encode isn't known before the time of manufacture, or is known only after it has been substantially manufactured, e.g.:
  calibration is determined after the strips are made and then QC tested, and customer or regional demand is known after an order is received.
The challenge for manufacturers is how to encode information onto a test strip in a manner that is:
  Cost effective,
  Flexible and can be done after manufacture, or as one of the final steps of manufacture,
  Can be read and interpreted directly by a meter or similar apparatus, and
  Is reliable, safe, and robust.
Furthermore, if there is damage to the strip port connector (SPC) pins (bending, corrosion, dust/oil/blood preventing electrical contact), then there is risk of the meter not reading the encoded information correctly. Thus, having a meter that reads such codes for the user requires a reliable meter design.

Figure 1:
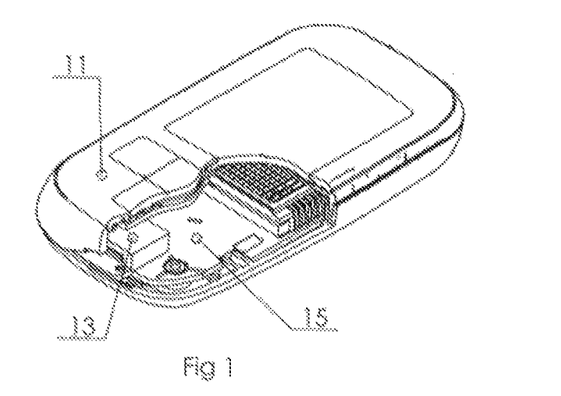
FIG. 1 shows a partial cut-away view of a test meter in accordance with the present invention.

The present invention provides an entire system to solve this, comprising:
  a strip port connector with additional pins that read a conductive pattern;
  conductive patterns that are designed to more safely encode information
  meter device intelligence to check if the SPC pins are not damaged and are making good contact
  strip notching and patterning methods to increase the number of available encoded configurations Test Meter of the Invention As depicted in FIG. 1, the basic structure of the test meter of the present invention comprises a housing 11 having a strip port connector 13. Electronic circuitry 15 is disposed within the housing 11. The strip port connect 13 is connected to the electronic circuitry and extends to an opening in the housing (i.e. fully or partially through the wall of the housing, or aligned with an opening in the wall of the housing) so that the strip port connector can connect the electronic circuitry with a received test strip. It will be appreciated that the meter depicted represents a minimum number of features, and that other features including displays, wired or wireless data transfer components, buttons, knobs and other user interfaces may be included in the meter as desired.

The strip port connector, its connection with the electronic circuitry, and its interaction with a received test strip incorporate various features as described below, which can be used individually or in any combinations of two or more of the features.

The strip port connector comprises at least one pair of top and bottom contacts. The reference to top and bottom contacts is arbitrary labeling, and does not define any specific relationship of the contacts with respect to gravity.

Figure 2:
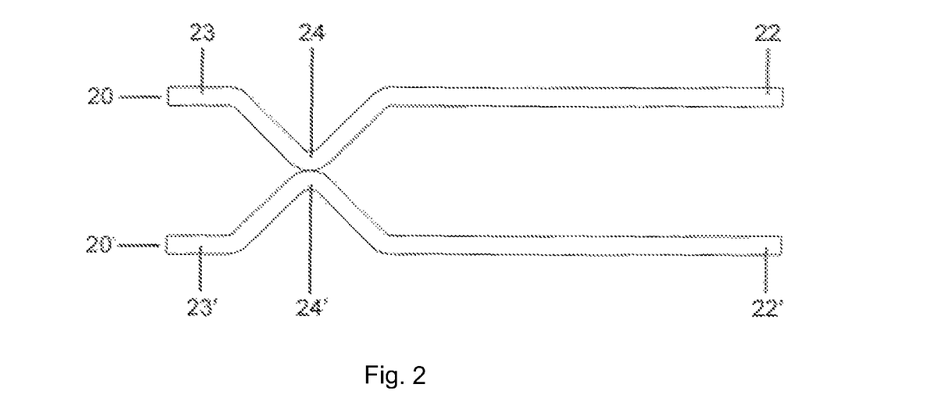
FIG. 2 shows a pair of contacts removed from a strip port connector in accordance with an embodiment of the invention.

FIG. 2 shows a side view of a pair of contacts, removed from the strip port connector of an embodiment of the invention. Each of the contacts 20, 20' have a proximal end 22, 22' through which connector to the electronic circuitry is made, a distal end 23, 23' and a central contact portion 24, 24'. The contacts as shown are flexible bent springs (for example flattened spring metal) which press towards one another as a consequence of the biasing force of the spring. In the assembled strip port connector, central contact portions 24, 24' make contact with each other as a consequence of the biasing of the springs. As used in the specification and claims of this application, the term "central contact portion" refers to the portions of the contacts that make electrical contact with one another as a consequence of this biasing, and does not require any specific position between the proximal and distal ends of the contact.

As used in the specification and claims of this application, the term "central contact portion" refers to the portions of the contacts that make electrical contact with one another as a consequence of this biasing, and does not require any specific position between the proximal and distal ends of the contact.

Figure 3:
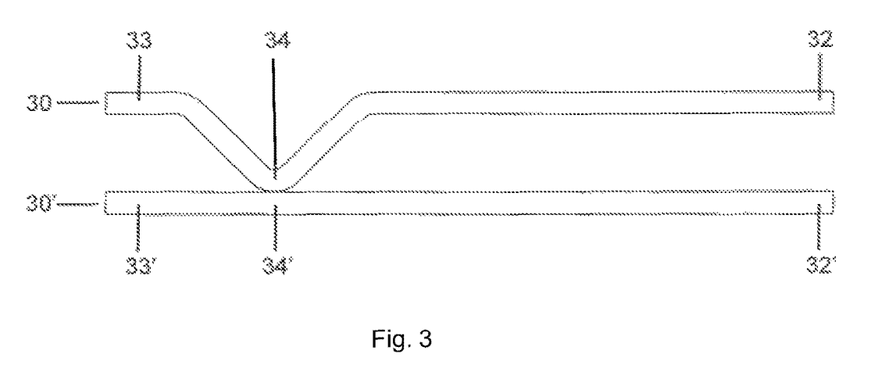
FIG. 3 shows a pair of contacts removed from a strip port connector in accordance with an embodiment of the invention.

FIG. 3 shows a side view of a pair of contacts, removed from the strip port connector of an embodiment of the invention. Each of the contacts 30, 30' have a proximal end 32, 32' through which connector to the electronic circuitry is made, a distal end 33, 33' and a central contact portion 34, 34'. In this embodiment, contact 30 is a flexible bent spring. Contact 30' is a flat contact pad when viewed from the side. In the assembled strip port connector, central contact portions 34, 34' make contact with each other as a consequence of the biasing of the contact 30.

Figure 16:
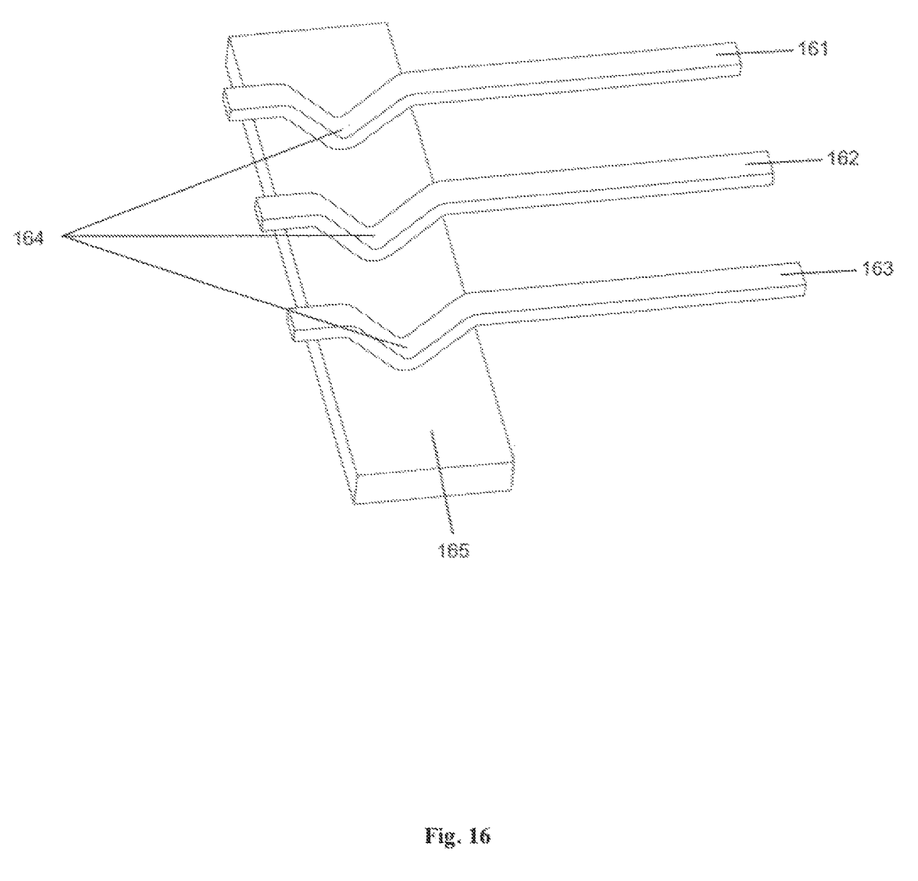
FIG. 16 shows an alternative set of contacts removed from a strip port connector in accordance with an embodiment of the invention.

FIG. 16 shows a variation of this design, for use when the desired goal is to confirm the integrity of the contacts and no encoding information needs to be obtained from the bottom surface of the test strip. This figure shows three "top" contacts 161, 162, 163, which are biased towards and make contact with a conductive plate. 165 when the strip port connector meets design specifications. Evaluation of the electrical connection between pairs of contacts 161/162, 161/163 and 162/163 allows a determination that all of the contacts are properly connected to the meter without requiring any direct connection from the plate 165 to the electronic circuitry. When a test strip is inserted into the strip port connector between the central contract portions 164 and the plate 165, the contacts 161, 162, 163 serve to provide the measurement signal, and may also as discussed below provide top surface encoding information.

Figure 4:
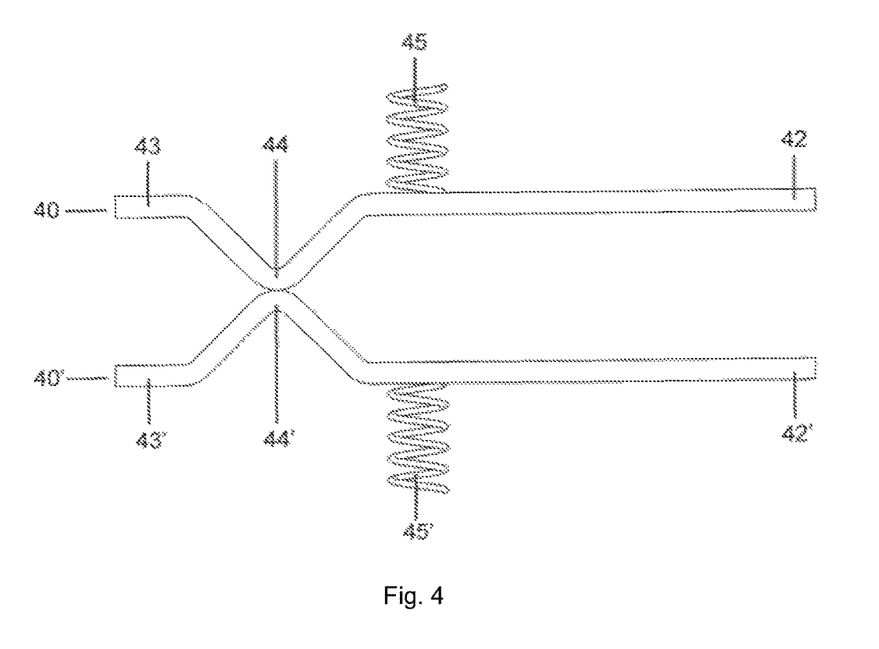
FIG. 4 shows a pair of contacts removed from a strip port connector in accordance with an embodiment of the invention.

FIG. 4 shows a side view of a pair of contacts removed from the strip port connector of an embodiment of the invention. Each of the contacts 40, 40' have a proximal end 42, 42' through which connector to the electronic circuitry is made, a distal end 43, 43' and a central contact portion 44, 44'.

Springs 45 and 45' bias the contacts towards one another when in the housing. In an alternative embodiment, the contact 40 and spring 45 can be combined with a flat contact pad as depicted in FIG. 3.

The top and bottom contacts are aligned at least transversely, that is, when viewed from above one of the contacts, there is a substantial or complete overlap with the width other contact, at least in the region of the central contact portion. Complete overlap or alignment is desirable, but is not required, so long as the extent of overlap is such that the electrical contact made between the central contact portions provides a robust and reproducible signal that can be used as an indicator of the correct positioning of the contacts within the strip port connector and that can be distinguished from the same type of signal (for example resistance or current) obtained when the strip port connectors have been unacceptably bent or damaged.

In some embodiments of the invention, the electronic circuitry tests for electrical contact between the pair of top and bottom contacts at one or more times when a test strip is not received in the test meter. This testing can be performed a predetermined number of times per day, for example 1, 5, 10 or 24 times per day; at predetermined time intervals, for example every 5 minutes, every 30 minutes or every hour; and/or it can be performed immediately following removal of a test strip from the strip port connector (for example within 5, 10, 30 or 60 seconds after removal). Based on the results of these tests, the electronic circuitry may generate an error state if the extent of electrical contact between the top and bottom contacts in the absence of a received test strip fails to meet a predefined threshold condition. The numerical value of the threshold depends on the specific parameter indicative of contact that is tested (current, potential, or resistance for example) the type of materials used to make the contacts, and the tolerances considered acceptable in view of the size of the contacts and other instrument parameters. By way of example, the threshold could be determined to be 5, 10, 20, 30, 40 or 50% different (above or below depending on the test performed) from the value expected if the contacts were positioned to design specifications within the strip port connector.

Figure 6:
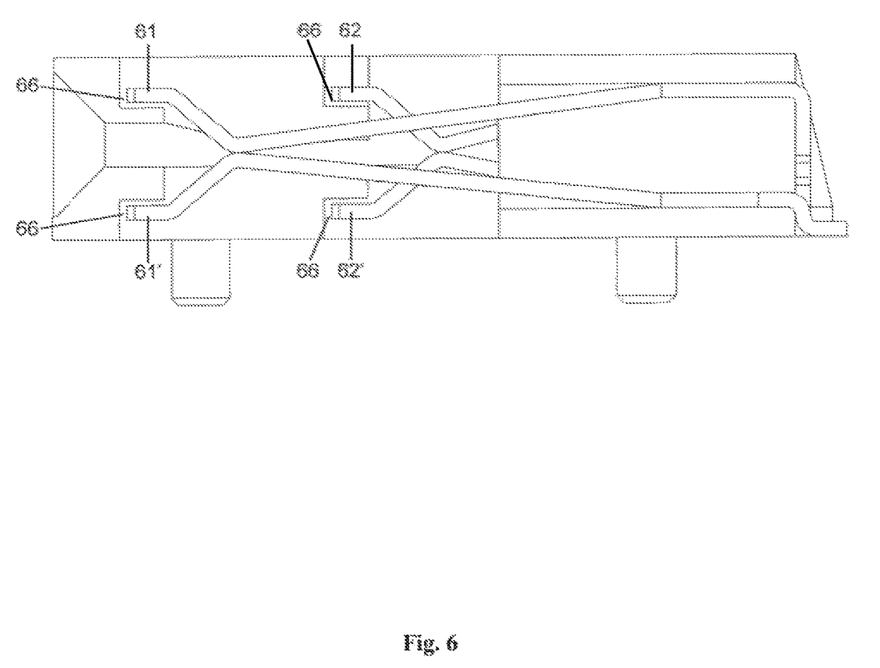
FIG. 6 shows a side view of a strip port connector.

FIGS. 2-4 show pairs of contacts in which the central contact portions are longitudinally aligned as well as being transversely aligned. In some embodiments of the invention, however, one of the top and bottom contacts extends longitudinally within the strip port connector to a greater extent than the other. FIG. 6 shows a side view of a strip port connector showing one pair of contacts 61, 61' with longitudinal alignment, and one pair of contacts 62, 62' in which the contacts are longitudinally offset. In a strip port connector with a plurality of pairs of top and bottom contacts, the pairs may be all longitudinally aligned, all offset, or any mixture thereof.

Figure 7:
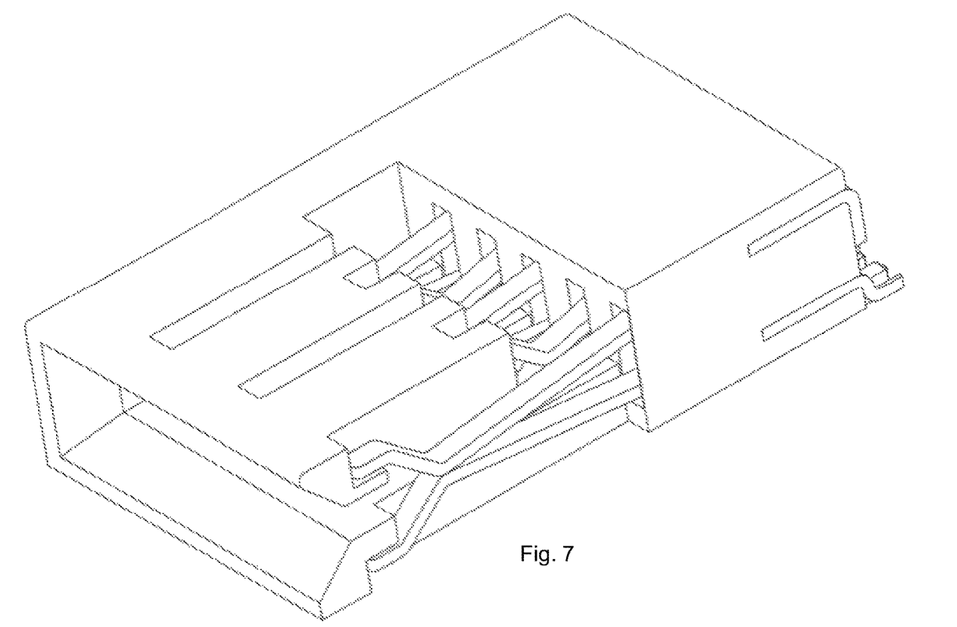
FIG. 7 shows a cut away perspective view of a strip port connector.
Figure 8:
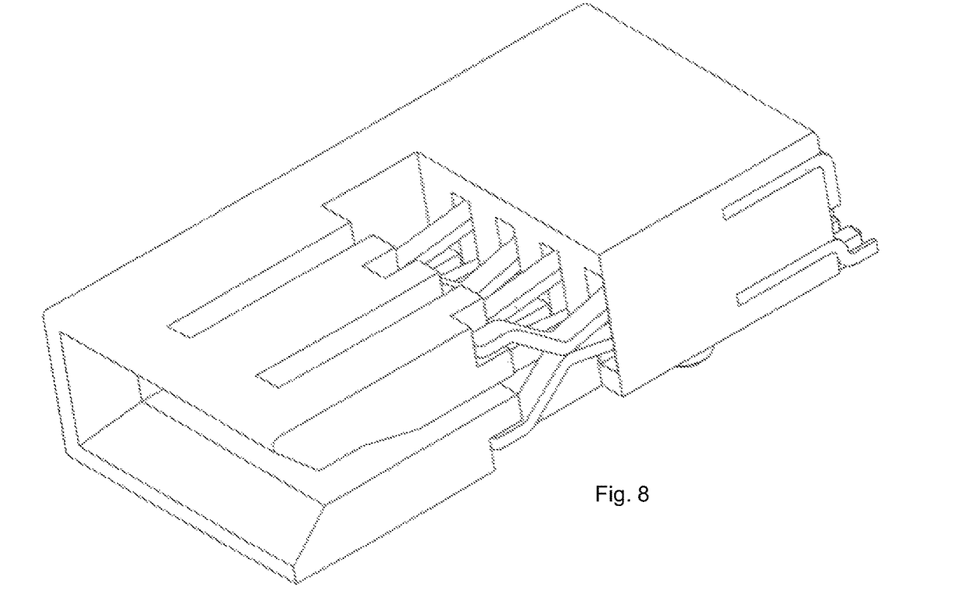
FIG. 8 shows a cut away perspective view of a strip port connector.

As further illustrated in FIG. 6, when the meter contains a plurality of pairs of top and bottom contacts, some of the contacts may have a first longitudinal length between the proximal end and the contact region of the central portion, and others may have a second longitudinal length, different from the first longitudinal length, between the proximal end and the contact region of the central portion. Thus, pair 61, 61' is longer in longitudinal length than pair 62, 62'. When more than two pairs of top and bottom contacts are present in a strip port and these include contacts of differing lengths, the pairs may be present in an ordered array, for example alternating arrays such as long-short-long-short; long-short-long-short-long; or short-long-short-long-short or some other pattern, for example long-long-short-long-long or long-long-short-short-long-long. FIGS. 7 and 8 show strip port connectors having four (two long, two short) and 5 (three long, two short) pairs of top and bottom contacts.

The flexible bent springs as illustrated in FIG. 6 applying a biasing force driving contact 61 towards contact 61' and vice versa. To limit the extent to which the distal end of the contact can be moved by this biasing force, a ledge 66 may be disposed adjacent to the distal end of the contact. The term "adjacent" means that the distal end is close to or in contact with the ledge under normal biasing conditions. The ledge(s) limits deflection so that different biasing force produced by two contacts in a pair does not distort the contact.

Figure 5:
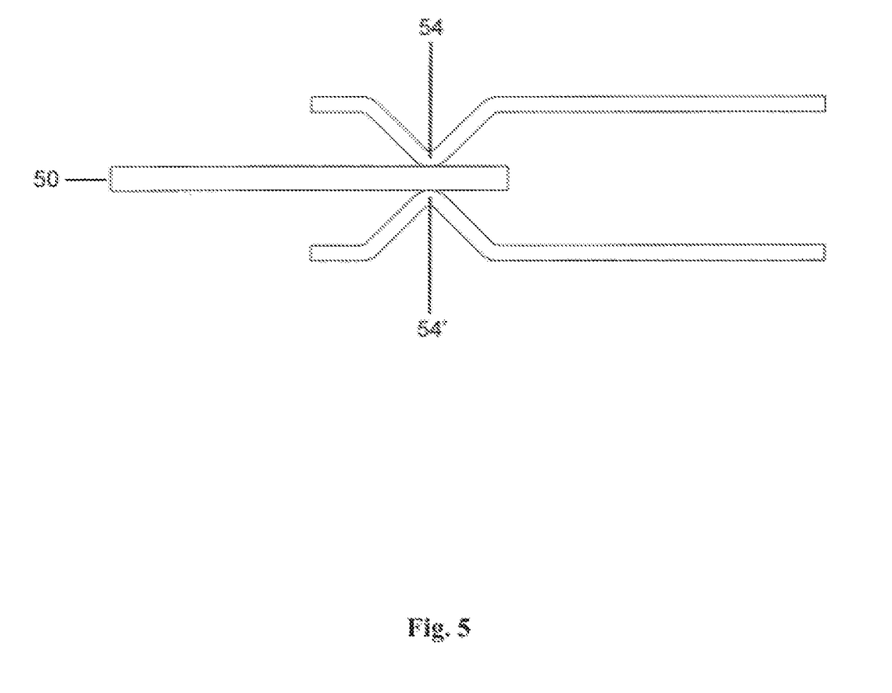
FIG. 5 shows a pair of contacts removed from a strip port connector in accordance with an embodiment of the invention with a test strip insert therebetween.

The distal ends of the top and bottom contacts are separable from one another by insertion of a test strip 50 between the opposed contacts as shown generally in FIG. 5 using the structure of FIG. 2 as an example. This insertion results in the test strip 50 being located between the central contact portions 54, 54'. When the test strip 50 is inserted in the strip port connector in this manner, one surface of the test strip is in contact with the contact portion 54, while the opposite surface is in contact with the contact portion 54'. As a result, when a test strip is inserted in the meter, one of the contacts can be used to read encoding marks disposed on one surface of the test strip, while the other contact is used for receiving information from the analytical part of the test strip.

Figure 9:
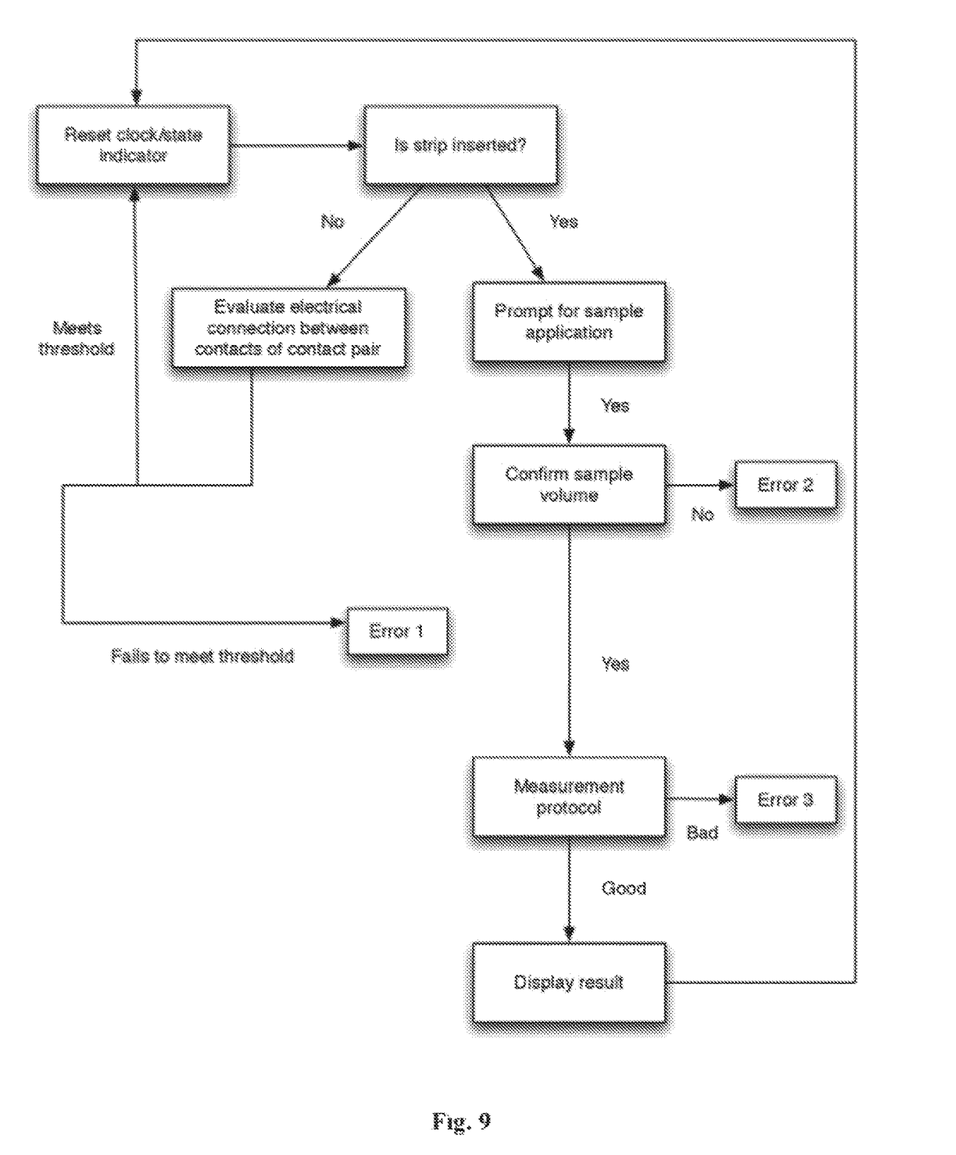
FIG. 9 shows a flow chart of the operation of the electronic circuitry in a meter in accordance with the invention.

FIG. 9 illustrates the electronic circuitry in a functional schematic diagram for one embodiment of the invention. As shown in FIG. 9, the electronic circuitry has two modes of operation: a no-strip mode, and a strip-inserted mode. In response to a signal, such as a clock signal or strip removal signal, a test is performed to determine if a strip is inserted. Various approaches are known in the art for detecting strip insertion including mechanical switches that are deflected by the insertion of a strip, measurement of changes in resistance when a strip is inserted, measurement of current when a strip is inserted and measurement of voltage when a strip is inserted. In the meter of the present invention, insertion can also be detected by the failure of connection between the contacts in a plurality of contact pairs in the strip port connector.

If strip insertion is not detected, the electronic circuitry proceeds to evaluate the electrical connection between contacts in contact pairs present in the strip port connector of the test meter. This can be done using any method that evaluates the quality of the electrical contact. When the contacts in the pair are in the desired spatial relationship and in contact with one another, they act like a switch in a closed circuit through which current can pass. Measurements of current (increased current means better contact) or resistance (high resistance means poor contact) or a potential difference (a difference in potential indicates poor contact) can be used by applying an appropriate input to a circuit containing the contacts in the pair.

If the observed result fails to meet the pre-determined measurement/device specific threshold conditions for one or more contact pairs, it is determined that the strip port connector is damaged and an error state (Error 1) is created. In the error state, the test meter may alert the user to check for complete insertion or the need for a new meter, and/or it may lock out the meter to prevent further measurements from being made. If the observed result meets the predetermined measurement/device specific threshold conditions, a clock/state indicator is reset that defines the next time interval or event at which the next strip insertion check is to be made.

When strip insertion is detected, the second branch of the flow chart of FIG. 9 is followed. In this protocol, the meter prompts the user to apply a sample and tests for the sufficiency of sample volume. If insufficient sample is present (or if a time out period elapses between insertion and sample application) an Error state (Error 2) is created. This does not lock out the meter permanently (as could Error 1), but would require a new strip insertion before a test could be run. If the sample volume is sufficient, then a measurement protocol is run. The term measurement protocol here refers to whatever procedures are performed in the test meter by the electronic circuitry to collect data about the analyte in the sample and make corrections to this data before displaying a result. Thus, measurement protocol includes the collection of measured data from the sample and any error correction procedures performed by the electronic circuitry, and may also include adjustment of this measured data to take into account encoded information such as calibration information if provided by the strip. If the result after any error checking included in the measurement protocol is a "good" test, then a result is displayed, and the clock/state indicator is reset to define the next time interval or event at which the next strip insertion check is to be made. If the result after any error checking included in the measurement protocol is a "bad" test, then an error state (Error 3) is created. Again, this would require new strip insertion before a new test can be run, but could provide additional information such as suggesting a new strip lot, as opposed to an indication of requiring more sample.

In the flow chart of FIG. 9 in the strip-inserted analyte assessment mode, it will be appreciated that not all of the steps listed are required. Thus, the meter need only perform the measurement protocol and somehow convey the results to a user or their health care professional. Numerous measurement protocols for analyzing input from a test strip are known in the art and can be used with the meter of the present invention.

In a further embodiment of the invention, the test meter is as discussed above while the top and bottom contacts are biased towards each other, the central contact portions of the contacts are close to but not in electrical contact with one another when no test strip is received in the test meter. The distal ends of the top and bottom contacts are separable from one another by insertion of a test strip between opposed contacts such that the central contact portions contact the received test strip. This does not allow the confirmation of contact integrity discussed above, but does allow one of the top or bottom contacts to be connected to the electronic circuitry to read encoding marks disposed on one surface of a test strip, and the other of the top or bottom contacts is connected to the electronic circuitry to obtain information about measurements made by the test strip on a sample introduced into the test strip.

Test Strip of the Invention

Test strips of the present invention are electrochemical, generally disposable test strips for the determination of one or more analytes in a sample. Exemplary analytes include glucose, ketones, lactate, cholesterol, hemoglobin and vitamin C. Such strips are known in the art, as is the concept of providing coded information about the strip through a marking on the test strip. This coded information can provide information about any of a number of features of the test strip, including by way of example, calibration code for a test strip batch, regional coding or country coding for the particular test strip, product identification to configure them to only work in their designated meter, customer identification, assay type (e.g. glucose test strip or ketone test strip), date of manufacture, expiration date, and the like.

Figure 10A:
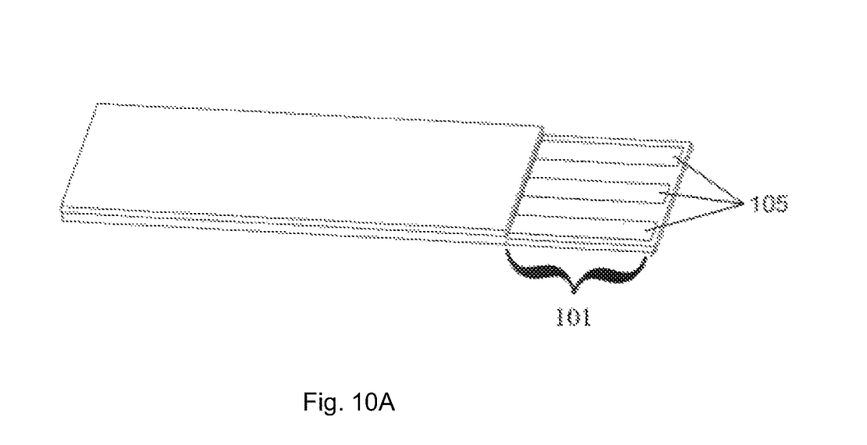
FIGS. 10A and 10B show top and bottom views of a test strip in accordance with the invention.
Figure 10B:
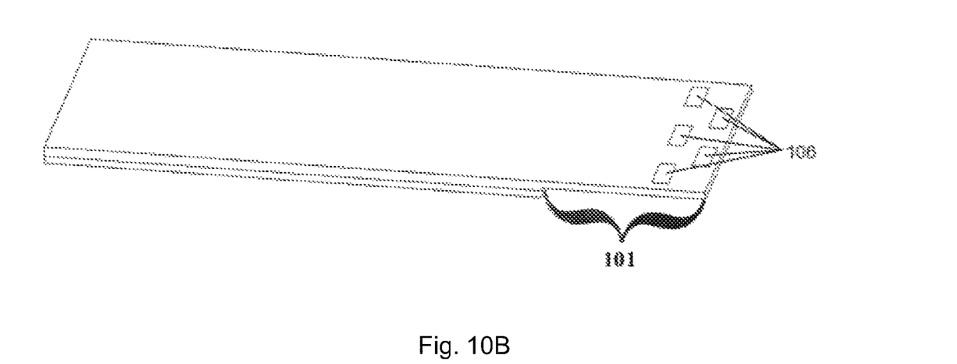

FIG. 10A shows a top view of a test strip in accordance with the present invention. FIG. 10B shows a bottom view. It will be appreciated that specifics of internal connections, analyte detecting chemistry, and sample chamber location and size are not critical to the practicing of the present invention and that these can take any of the numerous forms known in the art.

As shown in FIGS. 10A and 10B, the test strip is a generally planar elongated strip. At one end is a connector region 101 on which connector tabs 105 are disposed for making connection between a test meter and electrodes contained within the test strip. Three connector tabs are shown in FIG. 10A, but two connector tabs or more connector tabs could be used depending on the electrical connections to be made. These tabs are connected when the strip is inserted and provide information to the measurement protocol and optional steps described in FIG. 9.

FIG. 10B shows the reverse side of the test strip of the invention. As shown, a plurality of conductive encoding pads 106 are disposed in the connector region 101. These pads, by their number, position, material, size, shape and interconnection provide encoded information about the test strip on which they are placed. In particular embodiments, the conductive encoding pads may be connected in different combinations by the use of variable conductive tracks interconnecting the pads as discussed in more detail below.

The connector tabs, the conductive encoding pads and any conductive tracks are all formed from conductive materials, but different materials may be used for different conductive parts. The conductive materials may be metals, particularly silver, gold or platinum, or they may be formed by conductive inks, such a conductive ink comprising conductive material such as carbon, silver, gold, or palladium. The encoding pads may be formed in a step separate from the conductive tracks during the manufacturing process, with the tracks added after the information content to be encoded is determined. Process known for the deposition of electrodes and connective tracks, including printing (for example screen printing or ink jet printing), and laser ablation to expose an underlying conductive layer (or to remove a conductive layer) can be used in the manufacture of the test strips of the invention.

When a test strip in accordance with the invention is inserted into a test meter in accordance with the invention, the connector tabs 105 provide the information for the sample specific determination of analyte presence or concentration through one of the contacts in each pair (i.e., the top contacts). The encoding pads are interrogated through the opposing (bottom) contacts of each pair to provide strip specific information to assist in the presentation of accurate test results with minimum user intervention.

Figure 11A:
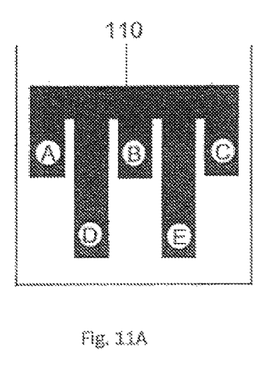
Figure 11B:
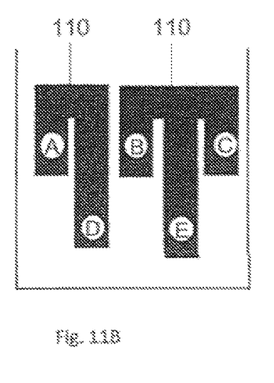
Figure 11C:
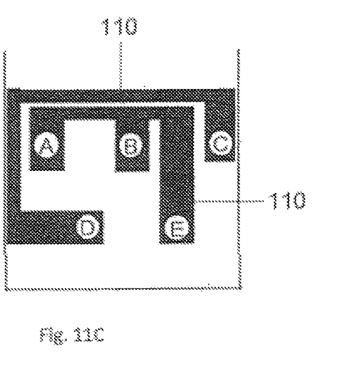

FIGS. 11 A-C show conductive patterns that can be utilized for the encoding pads 106 in test strips according to the invention. In these patterns every contact point/pin (A, B, C, D and E) is in electrical connection with at least one other contact point/pin when the strip is inserted (i.e., no single pin is left unconnected via a conductive trace) via conductive track 110. This is preferred if the test meter does not test for electrical connection between the top and bottom contacts in a no-strip state, because if there is damage to a pin, the lack of contact may be incorrectly interpreted as a lack of a conductive pattern at that contact point. This enhances the safety of the meter since an incorrect determination of the encoding pattern could produce a coding error, and therefore an incorrect result from a damaged contact/pin.

Figure 12A:
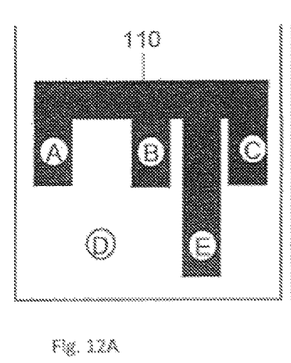
FIGS. 12A and B show embodiments of conductive patterns that can be utilized for the encoding pads 106 in test strips according to the invention.
Figure 12B:
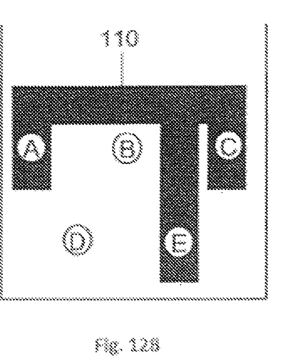
Figure 13A:
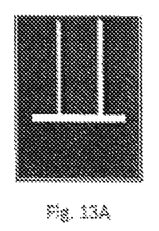
Figure 13B:
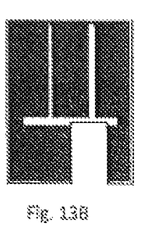
Figure 13D:
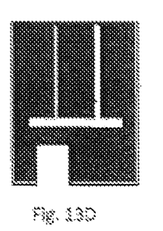

FIGS. 12A and B show additional embodiments of conductive patterns that can be utilized for the encoding pads 106 in test strips according to the invention. In FIG. 12 A, contact/pin D is not connected electrically to the remaining contacts/pins. In FIG. 12 B, contacts/pins B and D are not connected electrically to the remaining contacts/pins. This increases the number of coding options, but increases the possibility of error due to bent or missing pins unless the meter design discussed above is employed to test for contact/pin alignment.

Table I illustrates how the five contacts of FIGS. 11A-C and 12 A-B can display distinct information for encoding purposes simply by measuring the electrical connection between different contacts/pins.

If there is a notch in the strip, then at least one of the opposing pin pair may not get pushed apart. The meter can detect this state since there will be conduction between the top and bottom pins in the notched location. This then allows for a second set of encoded information to be determined by the meter when it is in this state, thereby increasing the number of different configurations that the meter can distinguish. Notching of this type for encoding purposes is disclosed in commonly assigned US Publication No, US 2009-0095623 A1, which is incorporated herein by reference.

Figure 14:
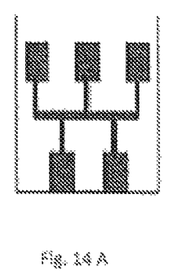
Figure 14B:
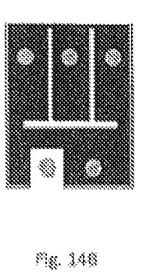
Figure 14C:
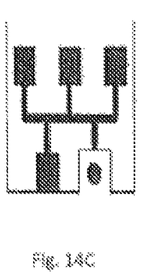

FIG. 14A shows a pattern of 5 encoding pads on the bottom surface of a test strip. FIG. 14B shows the top side of the connection region of this test strip with a notch cut out isolating one contact/pin. FIG. 14C shows the bottom side of the connection region of this test strip with a notch cut out isolating one contact/pin. The circles represent the connection points of the contacts in the test meter. As shown, one pair of contacts/pins do not touch the strip at all but rather remain touching each other. This reduces the available number of conductive configurations that can be utilized in the underside print, however, it allows the meter to distinguish (e.g. by detecting that one pair of pins is still in contact with each other) between the state where there is no notch (and therefore can utilize all five underside pins for encoding configuration) and the notched state (where the meter can utilize four of the underside pins for encoding configuration). This increases the number of encoding configurations available without the cost of adding additional contacts to the meter.

TABLE 1

| Figure | A-B | A-C | A-D | A-E | B-C | B-D | B-E | C-D | C-E | D-E |
|--------|-----|-----|-----|-----|-----|-----|-----|-----|-----|-----|
| 11A | Yes | Yes | Yes | Yes | Yes | Yes | Yes | Yes | Yes | Yes |
| 11B | No  | No  | Yes | No  | Yes | No  | Yes | No  | Yes | No  |
| 11 C | Yes | No  | No  | Yes | No  | No  | Yes | Yes | No  | No  |
| 12A | Yes | Yes | No  | Yes | Yes | No  | Yes | No  | Yes | No  |
| 12B | No  | Yes | No  | Yes | No  | No  | No  | No  | Yes | No  |

Yes indicates electrical contact is made between the contacts A-E; No indicates it is not.

By leaving other contacts/pins unconnected, additional unique patterns can be achieved. In addition, if the conductive tracks 110 are made from materials of different resistance, or changed in thickness or length to alter the resistance of the interconnections between the pads (contact points), another layer of information can be added including using the same five contacts/pins. Thus, observation of any current can be used to provide one set of information about the pattern of the contact pads, and the amount of resistance between pads can provide a different type of information. Use of more contacts/pins can further increase the amount of information.

Additional encoding information can also be provided through a combination of conductive encoding pads on the bottom of the test strip and conductive patterns on the top of the test strip. The top surface of the test strip has the usual electrical contacts for making connection to the electrodes in the electrochemical test cell, and the top contacts make contact with the top pattern. However, more encoding information is available if the top side pattern is exploited to provide more encoding configurations. Examples of this are shown in FIGS. 13A-D in which notches are omitted or included changing the connections between different parts of the conductive trace shown in black.

Figure 15A:
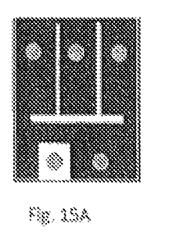
Figure 15B:
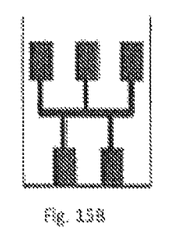

FIGS. 15A and B show an approach to achieving much the same effect without cutting an actual notch in the end of the test strip. In this case, a virtual notch is formed in the printed pattern around one of the contacts on the top surface (FIG. 15A). This allows all five of the pins to remain active for encoding on the bottom surface (15B) while creating a doubling of information by the isolation of the one contact/pin on the top surface. Similar multiplication can be achieved through the isolation of a different contact/pin, or more than one contact/pin on the top surface.

In the course of testing the strip port connector of the present invention, it was found that in some instances a user would insert a strip more than once, or move the strip in and out during the insertion process. As a result of this, some smearing of the conductive materials could occur, which could lead to unintentional contacts, and erroneous coding readings. To protect against such errors, it is desirable to configure the encoding pads and interconnecting conductors in such a manner that any smearing will not cross a conductive track. This is illustrated in FIGS. 17A-D.

Figure 17A:
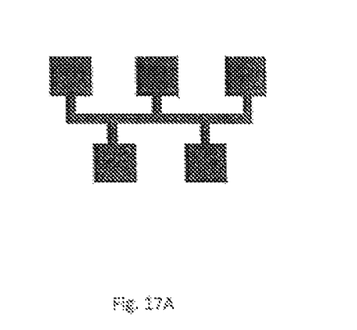
FIGS. 17A-D show encoding patterns and the effects of smearing.
Figure 17B:
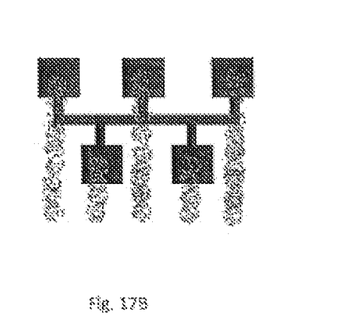
Figure 17C:
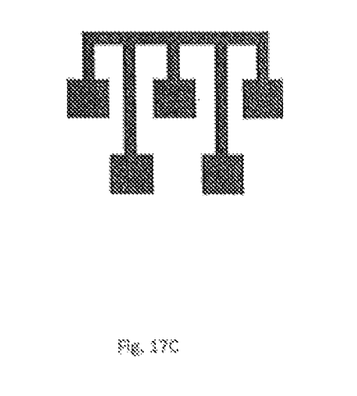
Figure 17D:
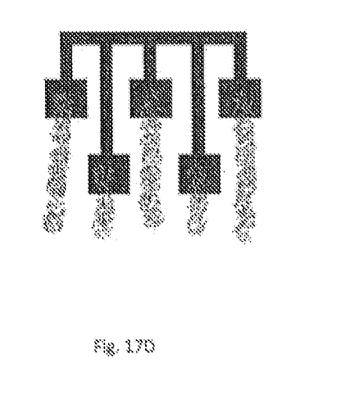

FIG. 17A shows a pattern of five encoding pads with connective tracks connecting them. FIG. 17B shows this same pattern with smear tracks. As can be seen, the smears can lead to connectivity between the three uppermost pads and the cross track, even if this was not intended. FIGS. 17C and D show a preferred configuration in which none of smear tracks (FIG. 17D) cross a conductive track. Therefore, if smearing of the material used to create the encoding pattern is a concern, a design of this type is preferred.

Combination of the Invention

A further aspect of the invention is a combination of a test meter as described above and a test strip as described above.

In some embodiments, the meter uses one member of each contact pair (i.e. the bottom contact) to read encoding pads disposed on the bottom surface of the test strip.

In some embodiments, the meter uses one member of each contact pair (i.e. the bottom contact) to read encoding pads disposed on the bottom surface of the test strip, and also a second member of some of the contact pairs (top contacts) to read additional coding information.

In some embodiments the meter uses one member of each contact pair (i.e. the bottom contact) to read encoding pads disposed on the bottom surface of the test strip and also recognizes notches cut in the test strip to isolate individual contact points and allow connection of a contact through the notch in the test strip to provide encoding information.

In some embodiments the meter uses one member of each contact pair (i.e. the bottom contact) to read encoding pads disposed on the bottom surface of the test strip and also recognizes a virtual notch that isolates individual contact points on the top surface of the test strip to provide encoding information.

Methods of the Invention

In accordance with some embodiments, the invention provides a method for monitoring a test meter that receives an electrochemical test strip to confirm integrity of the contacts that make electrical connection to the electrochemical test strip. The meter comprises a strip port connector comprising a pair of top and bottom contacts, said top and bottom contacts having a proximal end and a distal end and a central contact portion. The top and bottom contacts of the pair are transversely aligned with one another and are biased such that the central contact portions of the contacts are in electrical contact with one another when no test strip is received in the test meter. The distal ends of the top and bottom contacts are separable from one another by insertion of a test strip between the opposed contacts. The method comprises the step of testing for electrical contact between the pair of top and bottom contacts at one or more times when a test strip is not received in the test meter. As discussed above,
wherein testing for electrical contact between the opposed contacts may be performed a predetermined number of times per day, for example 10 or 24 times per day; at predetermined time intervals, for example every 5 minutes, every 30 minutes or every hour, or immediately following removal of a test strip from the strip port connector. The method further may comprise the step of generating an error state if the extent of electrical contact between the top and bottom contacts in the absence of a received test strip fails to meet a predefined threshold.

In accordance with another embodiment of the invention, a method is provided for determining the concentration of an analyte in a sample comprising the steps of Inserting an electrochemical test strip for detecting the analyte as discussed above into a test meter as described above; introducing a sample into the test strip, measuring an initial value for concentration of analyte, and adjusting the initial concentration of analyte as needed based upon information conveyed by encoding pads on the test strip to determine the concentration of analyte in the sample. In specific embodiments, the analyte is glucose and the sample is blood or interstitial fluid.

In the present invention, the labels "top" and "bottom" refer to relative geometries, and do not depend on any specific orientation relative to gravity.

What is claimed is:

1. A combination of
   a test meter for receiving a test strip, comprising:
   a housing;
   electronic circuitry disposed within the housing; and
   a strip port connector connected to the electronic circuitry and extending to an opening in the housing, said strip port connector connecting the electronic circuitry with a received test strip,
   wherein the strip port connector contains a pair of opposed contacts, each contact having a proximal end, a distal end, and a central contact portion, and
   wherein the electronic circuitry is configured to test for electrical contact between the pair of opposed contacts one or more times when no test strip is received in the meter; and
   an electrochemical test strip, said test strip being generally planar and comprising a sample cell for receiving a test sample for analysis and electrodes disposed within the sample cells for performing an electrochemical assay, said test strip having a top surface and a bottom surface, wherein the test strip compromises a connection region and wherein the test strip further comprises:
   (a) electrical connectors for connecting the electrodes to a test meter, said electrical connectors being disposed within the connection region and exposed for connection on the top surface, and
   (b) a plurality of encoding pads disposed within the connection region on the bottom surface of the test strip, wherein at least two of the encoding pads are in electrical connection with each other.

2. The combination of claim 1, wherein there are five encoding pads on the bottom surface of the test strip.

3. The combination of claim 1, wherein all of the encoding pads are in electrical contact with one another.

4. The combination of claim 1, wherein a notch is cut from the test strip to electrically isolate one of the encoding pads from the other encoding pads.

5. The combination of claim 1, wherein additional coding information is provided on the top surface of the test strip.

6. The combination of claim 5, wherein at least one encoding pad is provided on the top surface in electrical isolation from other encoding pads on the top surface.

7. The combination of claim 1, wherein the top and bottom contacts are transversely aligned with one another.

8. The combination of claim 1, wherein the distal ends of the top and bottom contacts are separable from one another by insertion of the test strip between the opposed contacts.

9. The combination of claim 1, wherein one of the top or bottom contacts is connected to the electronic circuitry to read encoding marks disposed on one surface of a test strip and the other of the top or bottom contacts is connected to the electronic circuitry to obtain information about measurements made by the test strip on a sample introduced into the test strip.

10. The combination of claim 1, wherein the top and bottom contacts are biased towards each other such that the central contact portions of the contacts are close to but not in electrical contact with one another when no test strip is received in the test meter.

11. The combination of claim 1, wherein the pair of contacts comprises a top contact and a bottom plate, and the top contact is biased such that the central contact portions of the contacts are in electrical contact with one another when no test strip is received in the test meter.

\* \* \* \* \*